United States Patent [19]

Nerad et al.

[11] Patent Number: 4,755,297

[45] Date of Patent: Jul. 5, 1988

[54] CONTINUOUS COUNTERCURRENT MEMBRANE COLUMN FOR THE SEPARATION OF SOLUTE/SOLVENT AND SOLVENT/SOLVENT SYSTEMS

[75] Inventors: Bruce A. Nerad, Longmont; William B. Krantz, Boulder, both of Colo.

[73] Assignee: University Patents, Inc., Westport, Conn.

[21] Appl. No.: 931,328

[22] Filed: Nov. 14, 1986

[51] Int. Cl.⁴ ............................................. B01D 13/00
[52] U.S. Cl. .................................... 210/637; 210/641; 210/321.65
[58] Field of Search .................. 55/16, 158; 210/636, 210/411, 641, 637, 321.65, 321.66

[56] References Cited

U.S. PATENT DOCUMENTS

3,144,313  8/1964  Pfefferle .............................. 55/16
3,505,215  4/1970  Bray .................................... 210/636
4,478,719 10/1984  Michele et al. ...................... 55/16 X Primary Examiner—Frank Spear
Attorney, Agent, or Firm—George M. Yahwak

[57] ABSTRACT

A reverse osmosis membrane process or hybrid membrane - complementary separator process for producing enriched product or waste streams from concentrated and dilute feed streams for both solvent/solvent and solute/solvent systems is described.

11 Claims, 9 Drawing Sheets

CONTINUOUS COUNTERCURRENT MEMBRANE COLUMN FOR THE SEPARATION OF SOLUTE/SOLVENT AND SOLVENT/SOLVENT SYSTEMS

The present invention lies in the general area of membrane separations technology and specifically that technology involving reverse osmosis. Reverse osmosis is a process in which an externally applied pressure is used to reverse the normal osmotic flow across a semipermeable membrane of one or more components in a solute/solvent (that is a mixture of two or more components which exists as a single phase liquid solution only over a limited concentration range, for example, an aqueous solution of an inorganic salt such as sodium chloride), or solvent/solvent (that is a mixture of two or more components which exists as a single phase liquid solution over the entire concentration range, for example, an aqueous solution of a low molecular weight organic such as ethanol) system.

Conventional reverse osmosis membrane separation processes involve the indirect contact of a high osmotic pressure solution (relative to the more permeable component) of one or more components osmotic pressure solution on the high pressure side of an appropriately selected semipermeable membrane with a low (relative to the more permeable component) osmotic pressure solution of one or more components on the low pressure side of the membrane. The low osmotic pressure solution normally constitutes the solution which permeates under conditions such that the applied pressure across the membrane exceeds the osmotic pressure difference across the membrane. Conventional reverse osmosis techniques have provided an economic alternative to energy-intensive separations, processes such as distillation, for solute/solvent systems in which the high molecular weight solute component has a low permeability relative to the solvent, and in which the solvent is the desired product. The need to overcome large osmotic pressure differences across the membrane limits this technique to solute/solvent systems, and to obtaining only one highly enriched product stream.

Reflux reverse osmosis, also known as concentrate return reverse osmosis, was first proposed by Loeb and Bloch (*Desalination*, 13, 207 [1973]), and involves the countercurrent flow of the low and high osmotic pressure solutions on opposite sides of the membrane. It maintains the externally applied pressure within practical bounds by refluxing a portion of the concentrated effluent stream from the high to the low pressure side of the membrane in order to reduce the osmotic pressure difference across the membrane. This technique can produce only one highly enriched product stream, however, and relatively large amounts of product are lost to the waste effluent stream.

The continuous membrane column, patented by Hwang in 1982 (U.S. Pat. No. 4,212,755) is a variation of reflux reverse osmosis which employs reflux on both ends of the membrane column and introduces the feed on the high pressure side at some position intermediate between the two ends of the column. Whereas this column can produce a highly enriched effluent stream containing the less permeable components, it is incapable of producing a highly enriched effluent stream containing the more permeable components while maintaining practical economic pumping costs for solvent/solvent systems. This limitation stems from the unidirectional nature of semipermeable membrane separations; that is, any less permeable component passing through the membrane cannot be removed from the low pressure side of the membrane. Thus, the effluent stream from the low pressure side of the continuous membrane column may not be sufficiently enriched if the more permeable components constitute the product, or alternatively it may contain too great of a concentration of the product if the more permeable components constitute a waste stream. An additional deficiency of the Hwang column is that no provision is made for recycle of either the high or low pressure effluent streams from the column to a complementary separator in order to achieve additional enrichment, or to the reactor or process supplying the feed stream in order to ensure practical economic use of the waste stream. These considerations, for example, render the continuous membrane column impractical and uneconomical for concentrating the dilute aqueous ethanol solutions emanating, for example, from biomass technologies; the effluent stream from the low pressure side of any membrane selectively permeable to water, will still contain a considerable amount of ethanol which will be removed with the waste stream.

Thus, there exists the need for a reverse osmosis membrane process (or hybrid membrane/complementary separator process) which will produce one or more highly enriched product or waste streams from both concentrated and dilute feed streams for both solvent/solvent and solute/solvent systems. Such a membrane or hybrid membrane process should be configured to maintain practical economic operating pressures throughout the membrane column; should be properly interfaced with the reactor or process producing the feed stream or streams as well as with any complementary separations device used in conjunction with the membrane process in order to provide optimal overall economics; and should correct deficiencies in conventional systems. The present invention provides a separation system which meets these needs.

It is, therefore, an objective of the present invention to employ a reverse osmosis membrane process in order to produce one or more enriched product or waste streams from both dilute and concentrated feed streams constituting either a solvent/solvent or solute/solvent system.

It is a further objective of the present invention to employ product or waste stream reflux at either or both ends of a continuous countercurrent membrane separator in order to achieve the desired separation and to maintain practical operating pressures throughout the membrane separator.

It is a further objective of the present invention to interface the continuous countercurrent membrane column with the reactor or processes which are the source of the feed stream or feed streams and any complementary separations device used in conjunction with the membrane separator in order to achieve the desired separation of components in the product or waste streams.

It is a further objective of the present invention to demonstrate the separation of dilute or concentrated solutions consisting of essentially ethanol and water, emanating from biomass or other processes, into an enriched ethanol product stream and an enriched water waste or recycle stream.

It is still a further objective of the present invention to demonstrate the separation of dilute or concentrated solutions consisting of essentially isopropanol and water, emanating from propane hydration or other processes, into an enriched isopropanol product stream and a aqueous isopropanol waste or recycle stream.

In order to accomplish the objects of the present invention one or more continuous countercurrent membrane columns are configured in any one of seven ways depending on the following considerations: (1) whether the desired separation can be accomplished economically using a dual membrane column, that is one which employs a membrane selectively permeable to at least one of the principal components of the product stream and another which employs a membrane selectively permeable to at least one of the principal components of the waste or other product stream; (2) whether the reactor or process creating the feed stream or feed streams produces a dilute or nondilute feed stream or feed streams of the desired product component or components; (3) whether the membrane rejects the desired product component or components; and (4) whether is it economic to dispose of the waste stream or to recycle it back to the reactor or process which produces the feed stream without removing more of the product component or components from it. Both the methodology for choosing the appropriate continuous countercurrent membrane column configuration as well as the column configurations and their application to specific separations tasks are unique to the present invention.

The continuous countercurrent membrane column in any of the above-mentioned seven configurations employs hollow fiber or other semipermeable membranes which, by virtue of the low Reynolds numbers attainable in countercurrent flow in such membrane devices, minimize backmixing effects.

The present invention employs a membrane material in the column which is semipermeable for the solvent-/solvent or solute/solvent system to be separated. This membrane material need not necessarily have a high rejectivity for the less permeable component or components in order to obtain a highly enriched product or waste stream or streams with this invention. The possible use of only moderately rejecting as well as highly rejecting reverse osmosis membranes in order to obtain highly enriched product or waste streams is unique to the present invention.

Among the possible examples of hollow fiber membranes for use in the present invention (although hollow fiber membranes are preferred for use in the present invention, other membrane configurations may, of course, be adapted and employed) are the duPont B-9 and B-10 polyamide membranes. These membranes have moderate rejectivities for most aqueous organic compounds. Other possible examples of membranes for use in the present invention with better rejectivities than the duPont membranes are the Universal Oil Products RC-100 and the FilmTec FT-30 membranes. These membranes, however, are commercially available only as flat sheets. For the separation of ethanol from water, the best membrane tested to date has been the IRCHA polyarylamide flat sheet membrane (see R. Dick and G. Mavel, Proc. Fifth Inter. Alcoholic Fuel Symp., Auckland, New Zealand, May 1982). Unfortunately, this membrane is not commercially available.

The continuous countercurrent membrane column used in the present invention employs a high pressure pump or similar device in order to permit reverse osmosis and refluxing a portion of the effluent stream from the low pressure side of the membrane column to the high pressure side of the column. By doing this, it is possible to further enrich the effluent stream from the low pressure side of the column in the concentration of the more permeable component or components. All or a portion of the remainder of the effluent stream from the low pressure side of the column can be drawn off as a product or waste stream. All or a portion of the remainder of the effluent stream from the low pressure side of the column can also be recycled back to the reactor or process which serves as the source of the feed stream, or may be recycled to a complementary separator. Choosing the reflux ratio for the effluent stream from the low pressure end of the column and providing for possible recycle of a portion of this effluent stream to the reactor or process supplying the feed stream, or to a complementary separator, are unique to the present invention.

The continuous membrane column in the present invention also employs a valve, turbine, or other work-extracting device to lower the pressure of the high pressure side of the column in order to permit refluxing a portion of this stream to the low pressure side of the column, thus maintaining practical economic operating pressures in the column while producing one or more highly enriched product or effluent streams. All or a portion of the remainder of the effluent stream from the high pressure side of the column can be drawn off as a product or waste stream, can be recycled back to the reactor or process which serves as a source of the feed stream, or may be recycled to a complementary separator. Choosing the reflux ratio for the effluent stream from the high pressure side of the column and providing for possible recycle to the reactor or process supplying the feed stream or to a complementary separator, are unique to the present invention. The possible use of a turbine or other device to extract useful work from the column is also unique to the present invention.

The present invention also provides for introducing the feed stream or feed streams into the continuous countercurrent membrane column at a location (or locations) which is optimal both with respect to matching the feed composition as well as the feed stream pressure. Under most conditions, this would imply that the feed stream or feed streams would be introduced on the low pressure side of the membrane thereby reducing the number of high pressure pumps required.

Under conditions where one product stream and another product or waste stream are required, one of which is highly enriched in the more permeable component or components, the present invention allows for the optimal interfacing of the continous countercurrent membrane column with such a device such as an external distillation column. When the column is configured to interact with a complementary separations device, the present invention provides for the proper use of a recycle stream from the column to the separator in order to permit both to operate at their optimum economic reflux ratios or ratio of internal countercurrent flow rates. This interfacing of the continous countercurrent membrane column with a complementary separations device is also unique to the present invention.

The continuous countercurrent membrane column, is not of itself capable of economically producing more than one highly enriched effluent stream. Although refluxing permits obtaining an effluent stream highly enriched in the less permeable component or components, the unidirectional nature of reverse osmosis implies that an effluent stream highly enriched in the more permeable component or components, is not achievable without impractical uneconomic pumping power requirements. The present column, however, can be coupled with a device such as another continous countercurrent membrane column employing a membrane with complementary permeation/rejectivity characteristics, or a distillation column, in order to produce two highly enriched effluent streams. Therefore, the present invention constitutes five process configurations for employing reflux and recycle streams optimally in order to interface the column with the reactor or process supplying the feed and an external complementary separations device, such as another membrane column with a complementary membrane, or a distillation column, in order to produce two or more highly enriched effluent streams; The present invention also constitutes two process configurations for employing reflux and recycle streams optimally in order to interface the continuous countercurrent membrane column with the reactor or process supplying the feed in order to provide optimal use of any waste stream. The present invention also constitutes a methodology for selecting which of the seven process designs is appropriate to the particular feed concentration, membrane rejectivity and waste stream recycle characteristics. Each of these seven process schemes will be described in detail below, along with the appropriate methodology for selecting that particular process.

A greater understanding of these and other aspects of the present invention may be had by reference to the drawings in which.

Figure 1:
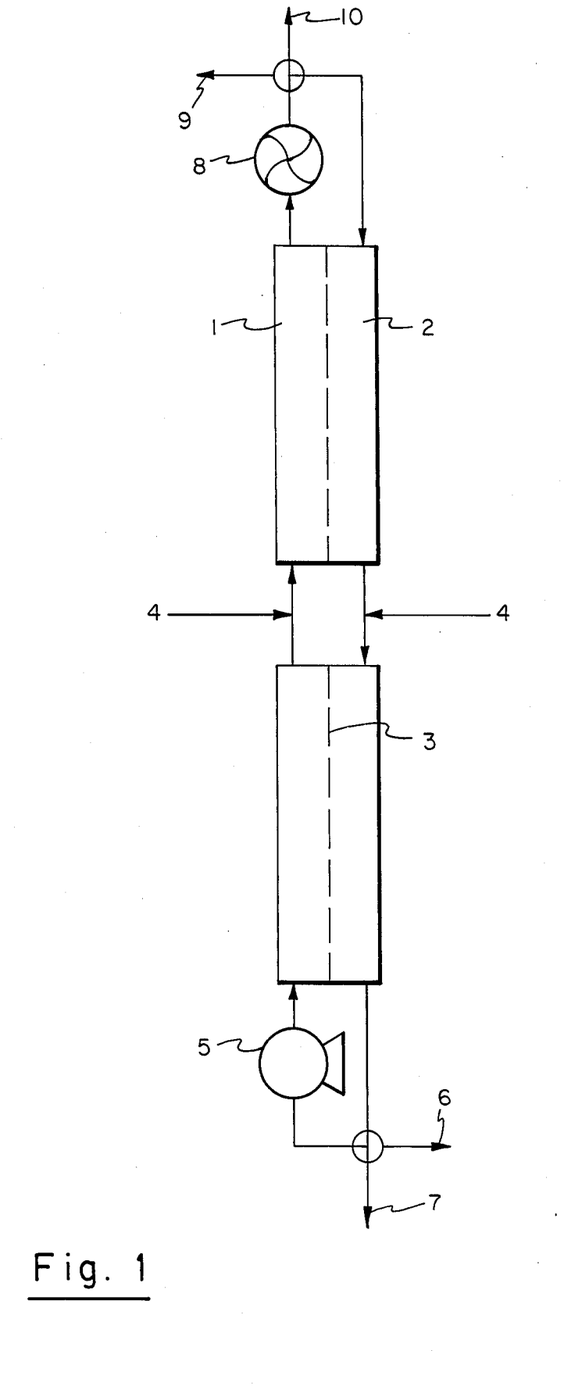
FIG. 1 is a schematic of a continuous membrane column according to the present invention.

More specifically, all seven of the membrane column configurations shown in FIGS. 3 through 9 employ one or more continuous countercurrent membrane columns shown in FIG. 1. With specific reference to FIG. 1, the continuous countercurrent membrane column 11 employs high pressure 1 and low pressure 2 sides separated by an appropriate membrane 3 chosen so as to minimize backmixing and to maintain reasonable pressure drops in the direction of high or low pressure stream flow on both sides of the membrane. This membrane could, in fact, constitute a hollow fiber membrane tube bundle or similar membrane configuration which maintains very low Reynolds number flow on both sides of the membrane so as to minimize backmixing. An advantage of the present invention is that the membrane also need not necessarily have a high rejectivity for one or more of the components in order to product one or more highly enriched product streams.

In use, the feed stream (or feed streams) 4 is introduced so as to match as closely as possible both the feed stream pressure and composition with the local pressure and composition of the liquid streams circulating in the continuous countercurrent membrane column. A pump or similar means 5 is employed to maintain a high pressure sufficient to cause reverse osmosis and to reflux a portion of the effluent stream from the low pressure side 2 of the column to the high pressure side of the column. A flow-control valve or similar means 6 is employed on the effluent stream coming off of the low pressure side of the column in order that a portion of this stream, enriched in the more permeable component(s) 7, can be continuously drawn off as a product or waste stream, or as a recycle stream to an external complementary separations means such as, for example, a distillation column. Alternatively this stream may be recycled back to the chemical reactor. A flow-control valve or similar means 9 is employed on the effluent stream 10 from the high pressure side of the column in order to reflux a desired portion of this stream to the low pressure side of the column. Subsequently, the pressure of the effluent stream leaving the high pressure side of the column is lowered by a work extracting device 8 which may be, for example, a turbine or a value which recycles energy back to the overall process per se, or which generates power for some extraneous nonprocess equipment. A portion 10 of the effluent stream from the high pressure side of the column, which is enriched in the component or components which is or are less permeable, is also drawn off continuously as a product or waste stream, or as a recycle stream to an external complementary separations means such as, for example, a distillation column. Additional product or recycle streams can also be drawn off, of course, at intermediate locations along either the high or low pressure side of the column.

Figure 2:
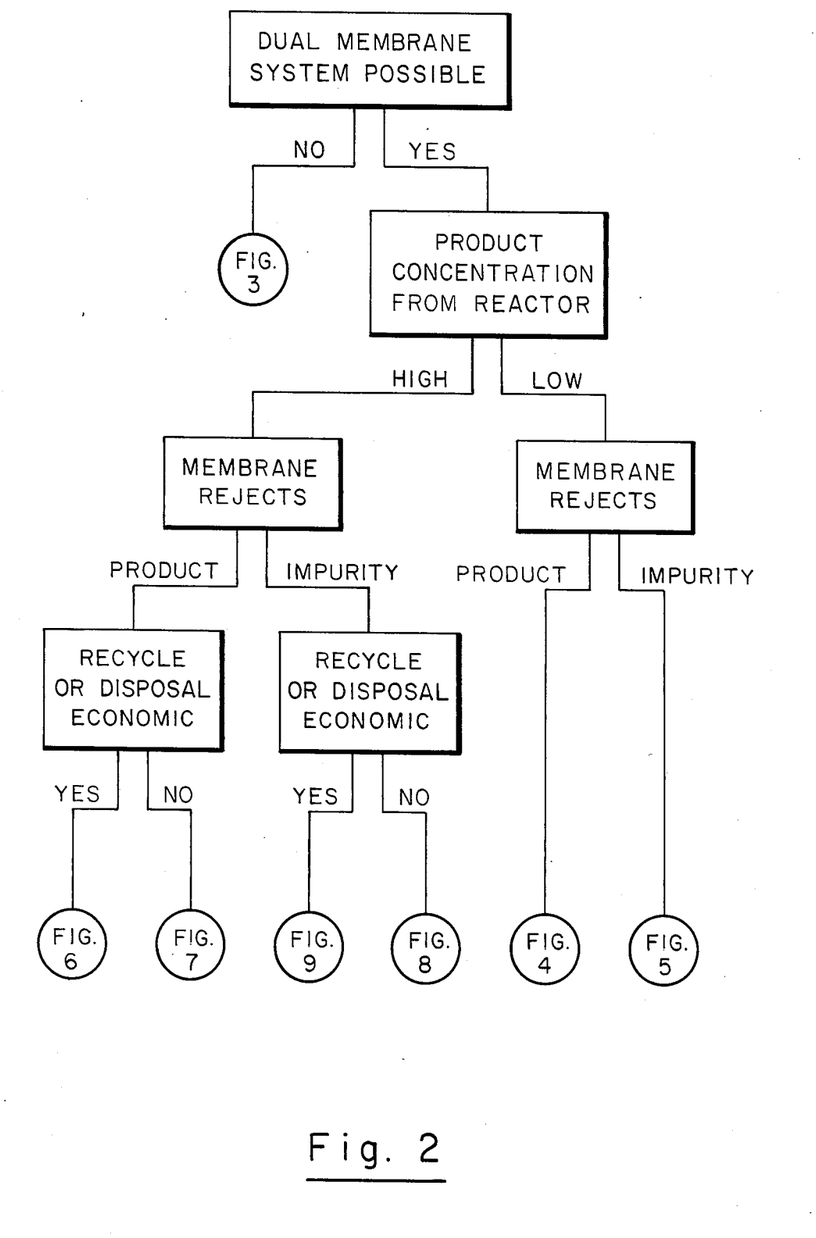
FIG. 2 is a flow chart for the integration of a continuous membrane column with a total separation system.
Figure 3:
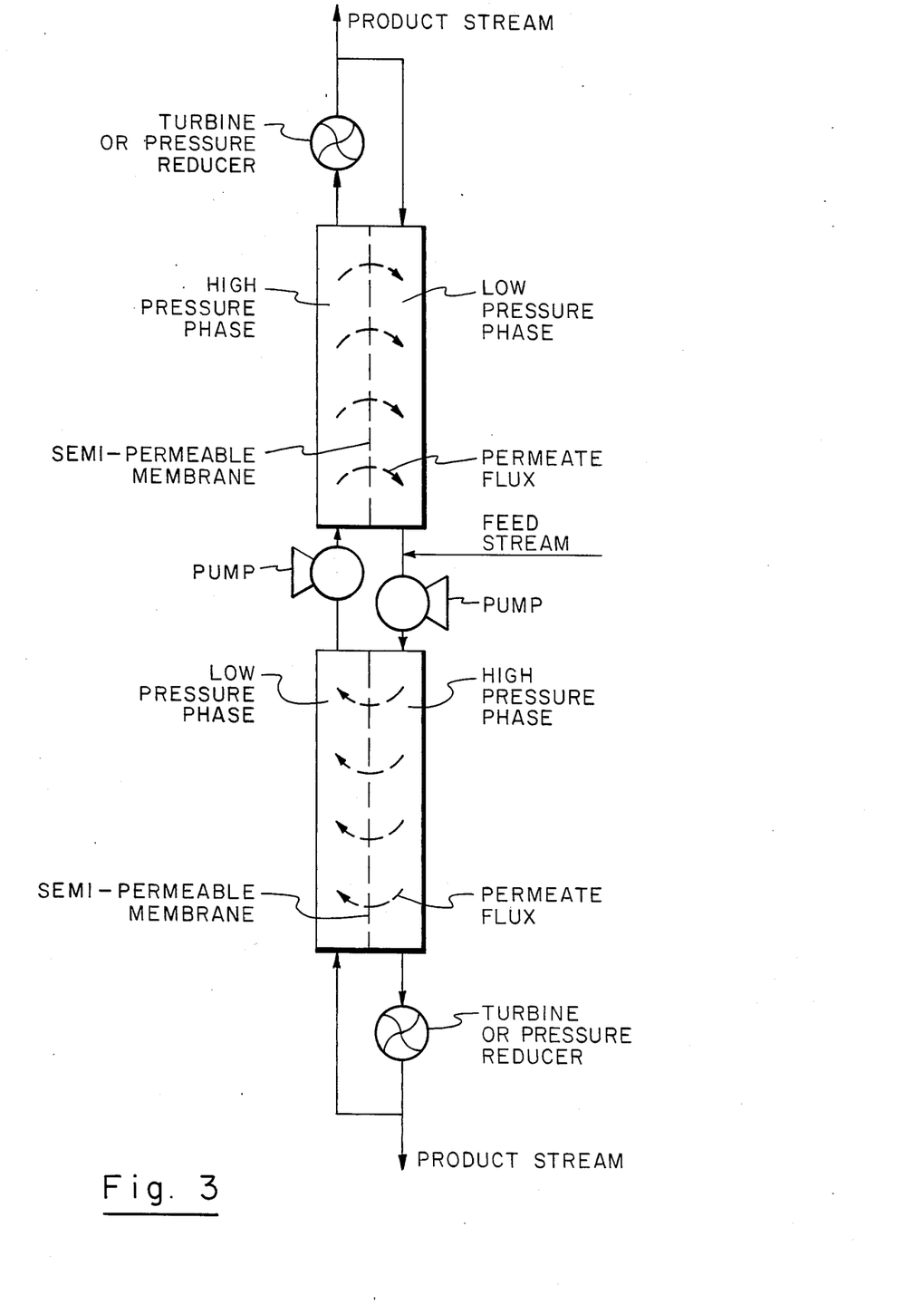
FIG. 3 is a schematic of a dual membrane separation system.

The continuous countercurrent membrane column selection methodology detailed in FIG. 2, indicates that one first consider whether the desired separation can be accomplished with a dual continuous countercurrent membrane column system. This dual system, as shown in FIG. 3, constitutes one or more columns of the type shown in FIG. 1 containing a membrane selectively permeable to the waste stream component or components, and one or more columns containing a membrane selectively permeable to the product stream component or components. The feed stream is introduced optimally into one of the two complementary columns. Two pumps or similar devices are employed to pump the effluent stream from the low pressure side of each column to the high pressure side of the complementary column. A portion of the high pressure effluent stream from each column is drawn off as a highly enriched product or highly enriched waste stream, whereas the remainder of each is refluxed to the low pressure side of each column, respectively.

The dual membrane system according to the present invention is used to separate a mixture into two enriched product streams. As depicted in FIG. 3, the dual membrane system requires two membranes; one which is permeable to one or more components, but not all of them, and a second membrane which is less permeable to the components which the first membrane permeates. For example, let us say that we have a mixture of A and B to separate. One membrane, located in the upper column, permeates A, and the other membrane, located in the lower column permeates B. The feed stream containing A and B enters the Dual Membrane System at the point that the low pressure effluent stream leaves the upper column. These streams mix, are pressurized by the pump and enter the high pressure side of the concentration of A increases as the fluid flows down the lower column. Upon exiting the high pressure side of the lower column, the pressure of this stream is reduced by, for example, a turbine. This stream is next divided into two portions. One portion being a product stream enriched in component A (relative to the feed stream). The other portion is refluxed to low pressure side of the lower column and serves to maintain the osmotic pressure difference between the high and low pressure sides of the lower column below the operating pressure of the system, i.e. the pressure developed by the pump. As the refluxed portion flows up the lower column, it becomes enriched in B, and exits the lower column, where before entering the upper column, its pressure is increased. Because the membrane in the upper column permeates A, the fluid becomes richer in B. Upon exiting the upper end of the upper column, the pressure is reduced and a portion of this stream is drawn off as a product stream enriched in B. The rest of this stream is refluxed to the low pressure side of the upper column in order to maintain the osmotic pressure difference of the upper column below the operating pressure. The refluxed portion flows down the low pressure side of the upper column and becomes increasingly concentrated in A and finally leaves the upper column, mixes with additional feed and the circuit around the column is complete.

Figure 4:
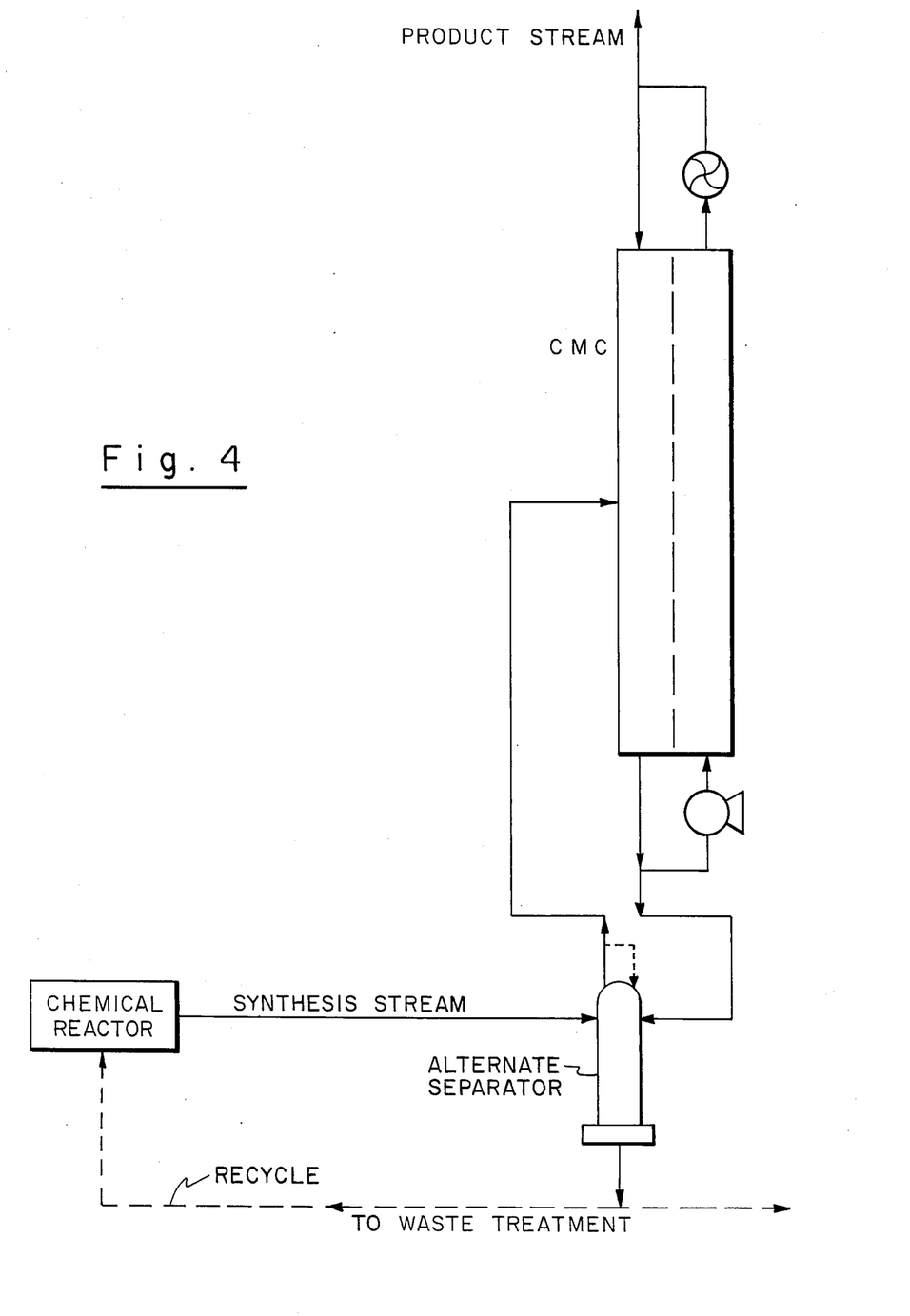
FIG. 4 is a schematic of an integrated separation system for a chemical reactor producing a low product concentration and for a membrane rejecting the product.

If a dual membrane column system is not feasible or practical, then the process selection methodology in FIG. 2 indicates one must consider whether the reactor or process produces a feed which is dilute or concentrated in the desired product component or components. If the feed has a low concentration of desired product components, and a membrane is available which is less permeable to these product components, the membrane column configuration shown in FIG. 4 is appropriate. Here a complementary separations device is required to produce an effluent stream highly enriched in the waste components. The dilute feed stream from the reactor is introduced optimally to a complementary separator. The effluent stream from the complementary separator which is highly enriched in the waste components is either disposed of or recycled back to the reactor. All or a portion of the stream concentrated in the product components is recycled as a feed stream to the column. The remaining portion of this stream, if any, is refluxed back to the complementary separator. A portion of the effluent stream from the low pressure side of the column is refluxed to the high pressure side of the column, and the remainder is recycled to the complementary separations device to serve as a second feed stream or as a reflux stream. A portion of the effluent stream from the high pressure side of the column is refluxed to the low pressure side of the column, and the remainder is drawn off as a highly enriched product stream.

Figure 5:
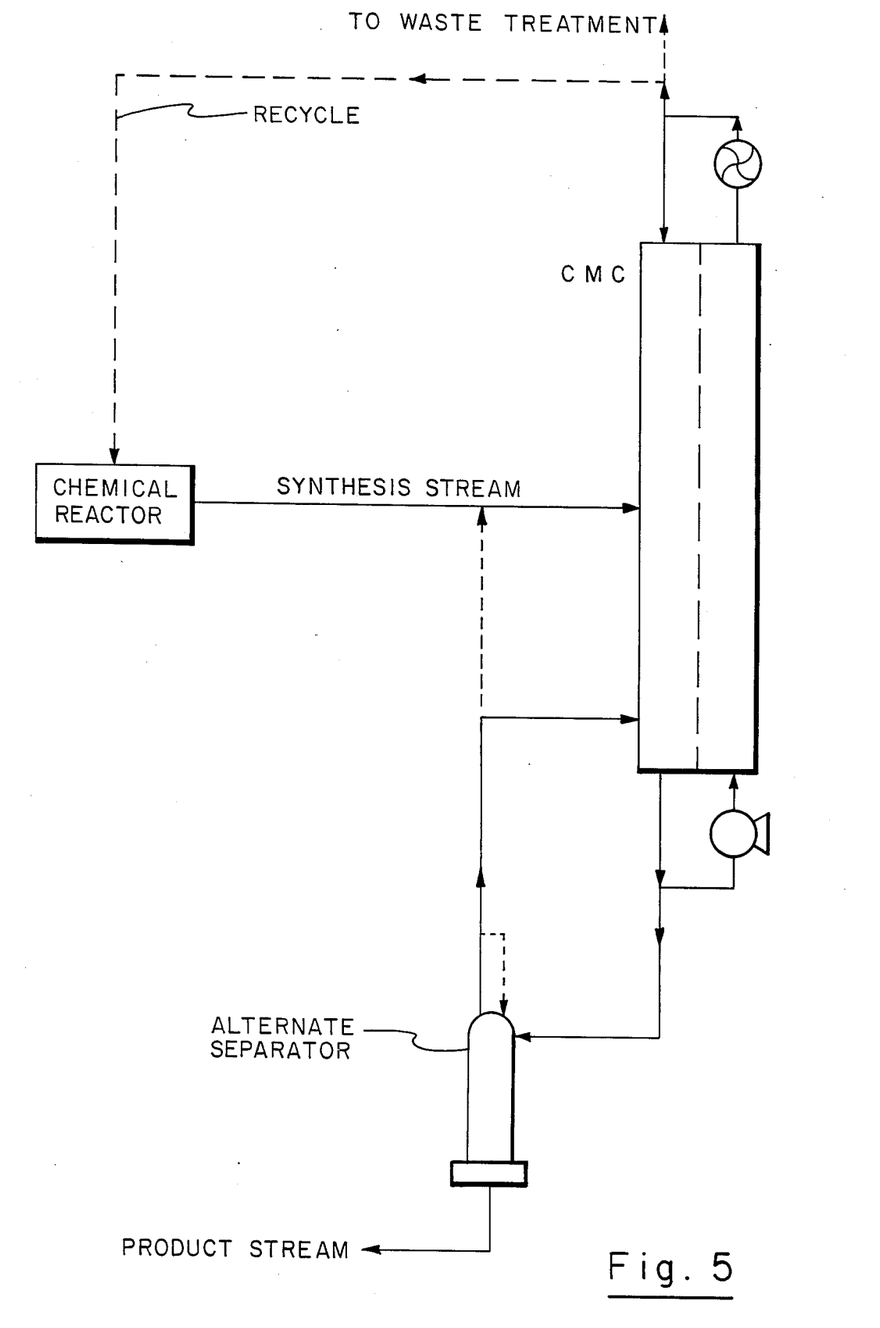
FIG. 5 is a schematic of an integrated separation system for a chemical reactor producing a low product concentration and for a membrane rejecting the impurity.

The process selection methodology in FIG. 2 indicates if the feed has a low concentration of the desired product components, but a membrane is available which is more permeable to these product components, the column configuration shown in FIG. 5 is appropriate. Here a complementary separations device is required to produce an effluent stream highly enriched in the product components. The dilute feed stream from the reactor is introduced to the column. A portion of the effluent stream from the high pressure side of the column is refluxed to the low pressure side and the remainder is drawn off as a waste stream which is either disposed of or recycled back to the reactor. A portion of the effluent stream from the low pressure side of the column is refluxed to the high pressure side, and the remainder is recycled to a complementary separator as a feed or reflux stream. All or a portion of the effluent stream from the complementary separator is recycled either to the primary feed stream or, as a second feed stream, introduced to the column. The remaining portion of this product-lean stream, if any, is refluxed back to the complementary separator. The other effluent stream from the complementary separator is drawn off as a highly enriched product stream.

Figure 6:
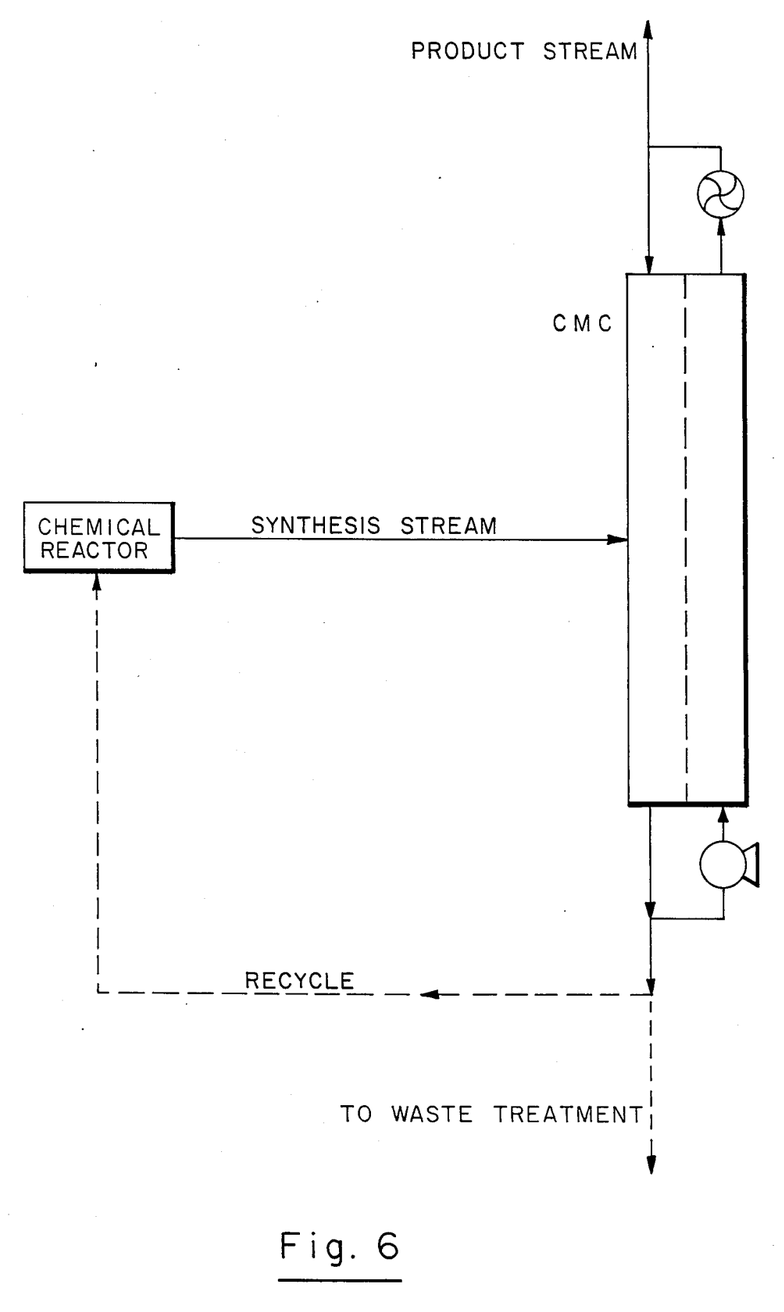
FIG. 6 is a schematic of an integrated separation system for a chemical reactor producing a high product concentration and for a membrane rejecting the product where disposal or recycle is possible.

The process selection methodology in FIG. 2 indicates if the feed has a high concentration of the desired product components and a membrane is available which is less permeable to these product components, and furthermore, it is economic either to recycle or dispose of the waste stream, then the membrane column configuration shown in FIG. 6 is appropriate. No complementary separator is needed to remove more product from the waste stream even though the latter is not highly enriched in the waste stream principal components. In this instance, the concentrated feed stream from the reactor is introduced to the continuous membrane column. A portion of the effluent stream from the low pressure side of the column is refluxed to the high pressure side, and the remainder is drawn off as a waste stream which is either disposed of or recycled back to the reactor. A portion of the effluent stream from the high pressure side of the column is refluxed to the low pressure side, and the remainder is drawn off as a highly enriched product stream.

Figure 7:
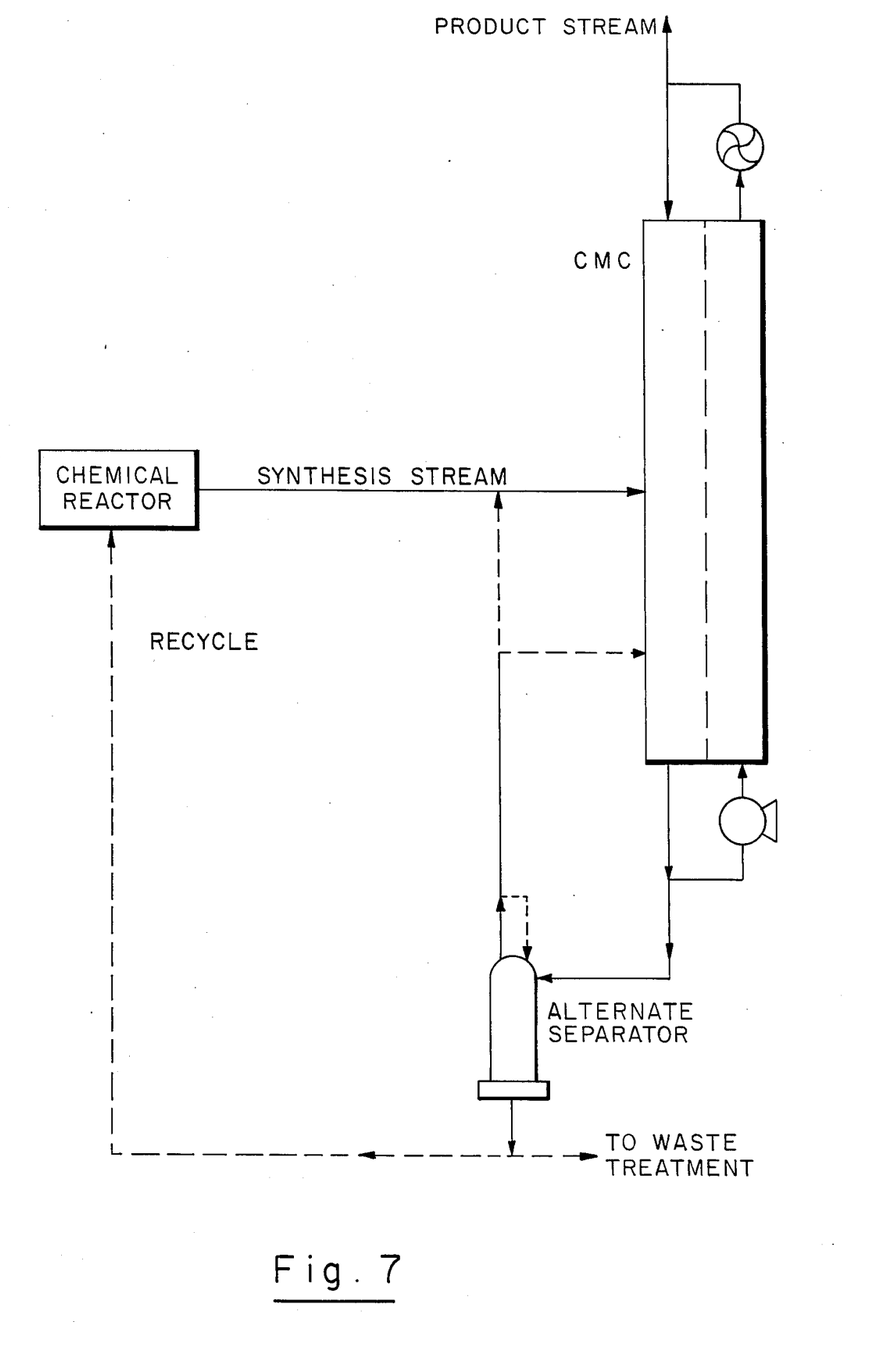
FIG. 7 is a schematic of an integrated separation system for a chemical reactor producing a high product concentration and for a membrane rejecting the product where disposal or recycle is not possible.

The process selection methodology in FIG. 2 indicates, however, if the feed has a high concentration of the desired product components and a membrane is available which is less permeable to these product components, but recycle or disposal of the waste stream is not economic, then the membrane column configuration shown in FIG. 7 is appropriate. In this configuration, a complementary separations device is required to produce an effluent stream highly enriched in the waste components. The high product concentration feed stream is again introduced optimally to the continuous countercurrent membrane column. A portion of the effluent stream from the low pressure side of the membrane column is refluxed to the high pressure side, and the remainder is drawn off as a recycle stream which is introduced optimally as a feed to a complementary separations device. All or a portion of the effluent stream from the complementary separator more rich in the product component, is recycled either to the primary feed stream or as a second feed stream introduced optimally to the column. The remaining portion of this product-rich effluent stream, if any, is refluxed back to the complementary separator. The other effluent stream from the complementary separator is drawn off as a waste stream which is either disposed of or recycled back to the reactor. A portion of the effluent stream from the high pressure side of the membrane column is refluxed back to the low pressure side, and the remainder is drawn off as a highly enriched product stream.

Figure 8:
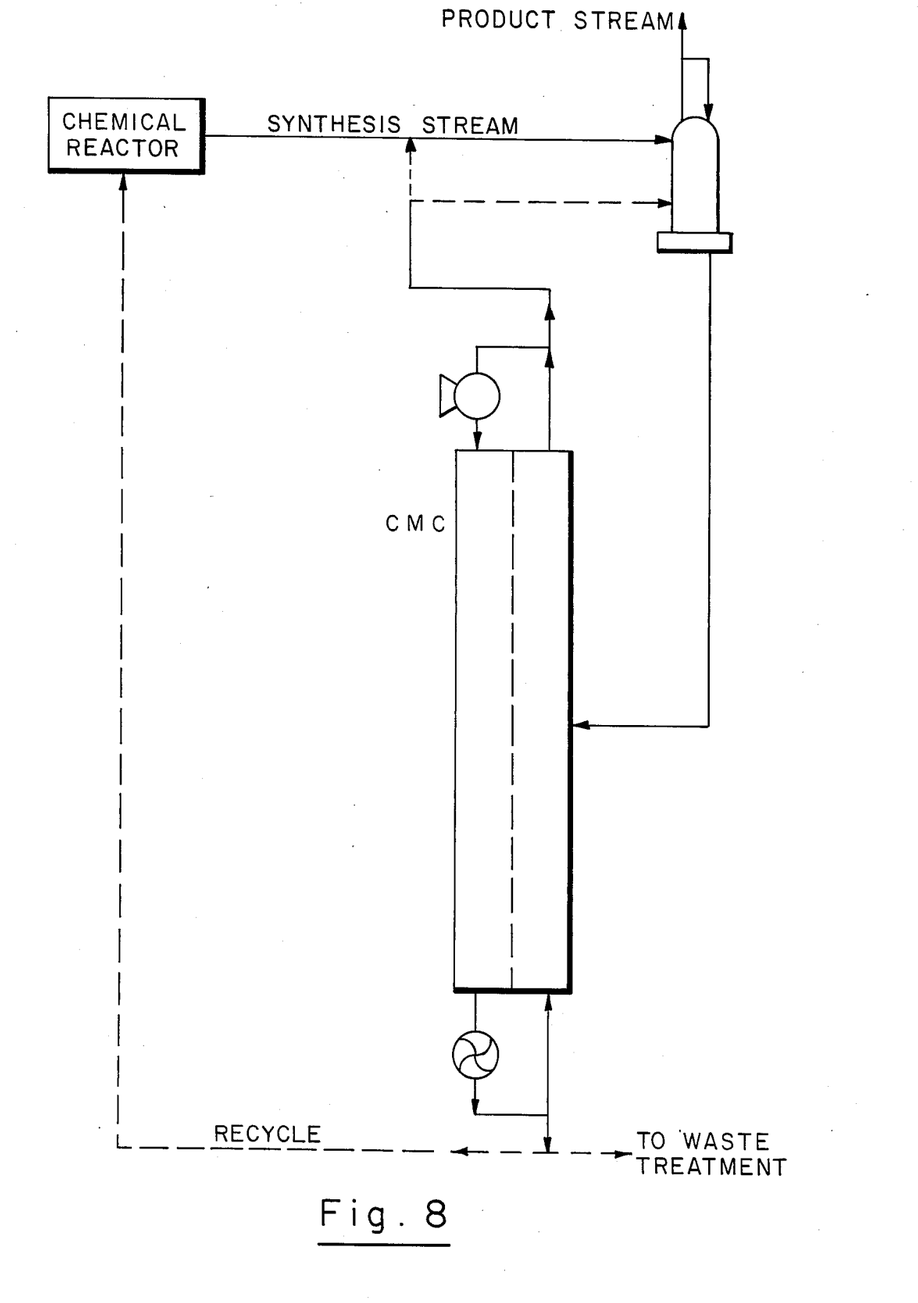
FIG. 8 is a schematic of an integrated separation system for a chemical reactor producing a high product concentration and for a membrane rejecting the impurity where disposal or recycle is not possible.

The process selection methodology in FIG. 2 indicates if the feed stream has a high concentration of the desired product components but a membrane is available which is more permeable to this product component and recycle or disposal of the waste stream is not economic, then the membrane column configuration shown in FIG. 8 is appropriate. In this instance, a complementary separations device is required to produce an effluent stream highly enriched in the product components. The high product concentration feed stream is introduced optimally to the complementary separator. The effluent stream from the complementary separator less rich in the product components is recycled as a feed stream which is introduced optimally to the column. A portion of the effluent stream from the high pressure side of the column is drawn off as a waste stream and either disposed of or recycled back to the reactor, while the remainder is refluxed to the low pressure side of the column. A portion of the effluent stream from the low pressure side of the column is refluxed to the high pressure side, and the remainder is recycled to the primary feed stream to the complementary separator or as a second feed stream introduced optimally to the complementary separator. All or a portion of the effluent stream from the separator highly enriched in the product components, is drawn off as a product stream, and the remainder, if any, if refluxed back to the complementary separator.

Figure 9:
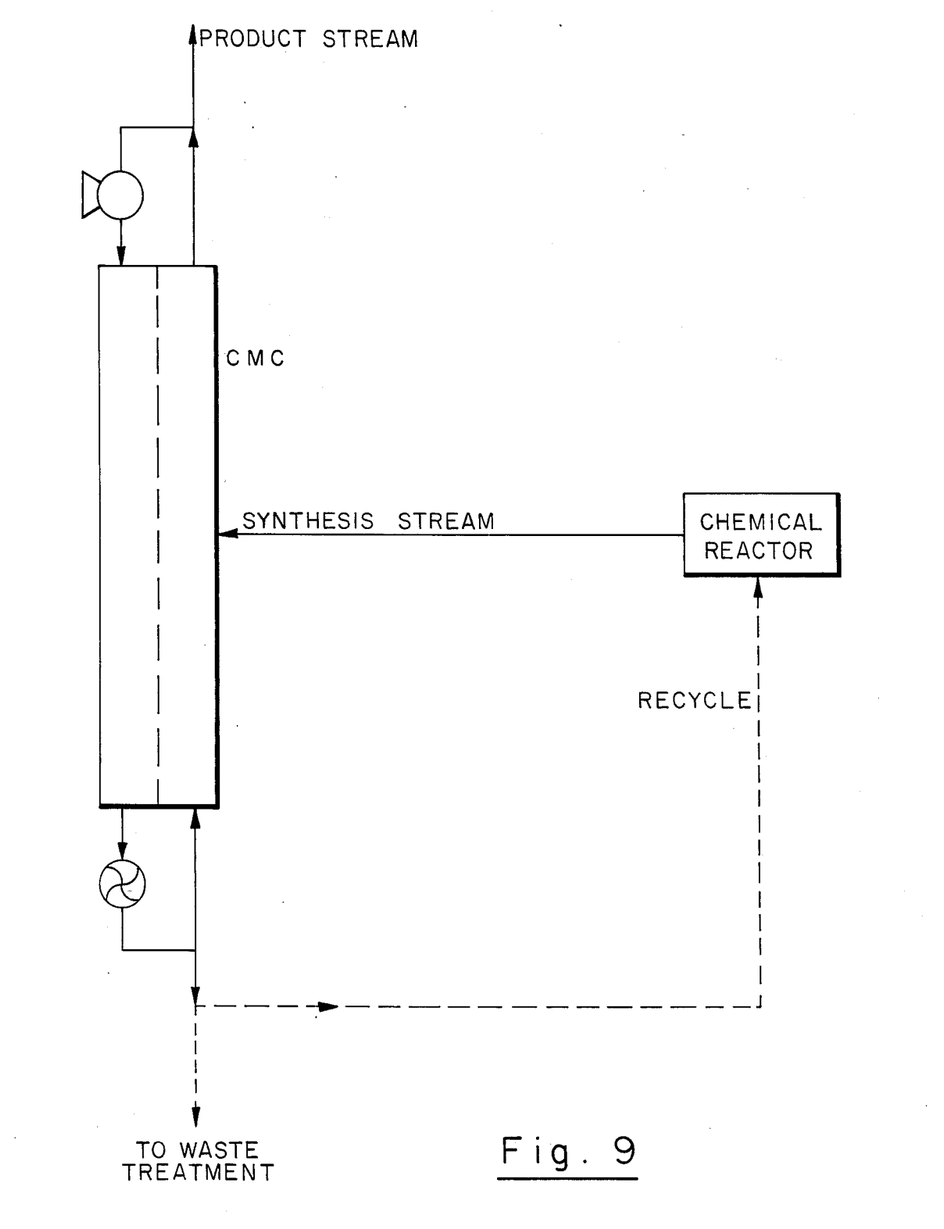
FIG. 9 is a schematic of an integrated separation system for a chemical reactor producing a high product concentration and for a membrane rejecting the impurity where disposal or recycle is possible.

The process selection methodology in FIG. 2 indicates if the feed stream has a high concentration in the desired product components and a membrane is available which is more permeable to these product components, and furthermore, it is economic either to recycle or dispose of the waste stream, then the membrane column configuration shown in FIG. 9 is appropriate. No complementary separator is needed to remove more product from the waste stream since it is assumed it is economic to lose some product in the waste stream even though the latter is not highly enriched in the waste stream principal components. In this instance, the high product concentration feed stream is introduced optimally to the membrane column. A portion of the effluent stream from the high pressure side of the column is refluxed to the low pressure side of the and the remainder is drawn off as a waste stream which is either disposed or of recycled back to the reactor. A portion of the effluent stream from the low pressure side of the column is refluxed to the high pressure side, and the remainder is drawn off as a highly enriched product stream.

If the product or waste stream of the membrane column configuration consists of two or more components, then this waste stream can be further separated into a second generation enriched product stream and waste or a second product stream by again invoking the appropriate methodology suggested by FIG. 2. In order to determine the appropriate methodology from FIG. 2, the product or waste stream from the first generation column configuration is considered to be the same as the feed stream from the chemical reactor or process. If recycle of a waste stream from the second generation membrane column configuration is economic, then this recycle stream is directed back to the chemical reactor or process supplying the feed stream or streams to the first generation membrane column configuration. In this manner, the methodology of FIG. 2 can be applied successively to separate the original feed stream or streams into the desired product and/or streams.

A. Production of an Enriched Ethanol Product from Dilute Aqueous Ethanol Feed Streams There is considerable need for technologies to produce motor-fuels grade ethanol from renewable resources such as waste or excess agricultural commodities. Biomass technologies are available for converting agricultural commodities into a dilute 3 to 6 mol percent aqueous ethanol solution. This dilute ethanol feed solution must be upgraded to 99 mol percent ethanol for motor-fuels purposes. Conventional or vapor-reuse distillation can be used to achieve the required enrichment at any energy consumption of 0.08 to 0.12 kW-h/mol of ethanol product. Since this energy consumption represents from 20 to 32 percent of the available heat of combustion of ethanol, appropriate membrane technologies offer the potential for considerable savings.

Since an application of this invention involves a feed stream which is dilute in the desired ethanol product, for which only membranes less permeable to the ethanol product are presently available, this implies that the continuous countercurrent membrane column configuration shown in FIG. 4 is appropriate. Here a complementary separations device is required in order to decrease the ethanol concentration in the waste stream sufficiently so that the nearly pure water waste stream can either be disposed of or recycled back to the biomass reactor to supply a portion of the water needed for hydrolysis.

A proof-of-concept evaluation of this column configuration indicates if a conventional distillation column is used to enrich a 3 mol percent aqueous ethanol feed stream to a 90 mol percent enriched ethanol effluent stream and nearly 0 mol percent waste or recycle stream, and a continuous countercurrent membrane column is used to enrich this 90 mol percent effluent stream to a 99 mol percent ethanol product using a modified DuPont B-10 polyamide hollow-fiber membrane module operating at a maximum pressure of 55 bar, the energy consumption is 0.07 kW-h/mol of ethanol product. In addition, the capital construction costs for this membrane column-conventional distillation hybrid process are estimated to be 37 to 50 percent less than those of conventional or vapor-reuse distillation processes for this same separation. If membranes such as the RC-100 developed by Universal Oil Products or the polysulfone-backed polyacrylamide membrane developed at the French Institute of Applied Chemical Research were to become available in a hollow-fiber module configuration, computer model simulations indicate the energy consumption could be reduced to as little as 0.025 kW-h/mol of ethanol product and the capital construction costs could be reduced by as much as 75 percent.

If membrane which permeate ethanol relative to water were used, then the membrane column configuration shown in FIG. 5 or FIG. 3 would be appropriate to enriching dilute aqueous ethanol feed streams to a highly enriched ethanol product.

B. Production of an Enriched Ethanol Product from Nondilute Aqueous Ethanol Feed Streams If a process or reactor produces a more concentrated aqueous ethanol feed stream which is to be enriched in ethanol, and presently available membranes are considered which are less permeable to ethanol, then the continuous countercurrent membrane column configuration shown in FIG. 6 is appropriate if disposal or recycle of a waste stream not highly enriched in water is economic, or FIG. 7 is appropriate if it is necessary to use a complementary separations device in order to remove sufficient ethanol from the waste stream to make disposal or recycle of this stream economic.

If membrane which permeate ethanol relative to water are used, then the membrane column configuration shown in FIG. 9 would be appropriate to enriching nondilute aqueous ethanol feed streams to a highly enriched ethanol product when disposal or recycle of a waste stream is economic; FIG. 8 would be appropriate to this separations task when disposal or recycle of a waste stream is not economic.

C. Production of an Enriched Isopropanol Product from Nondilute Aqueous Isopropanol Feed Streams Hydration of propylene to isopropanol, for example, produces a concentrated aqueous isopropanol solution which must be enriched to nearly pure isopropanol by an appropriate separations process. At present, only membranes are available which are less permeable to isopropanol relative to water. If recycle of the waste stream is economic, such as would be true for the propylene hydration process for the production of isopropanol since the reaction consumes water, then the continuous countercurrent membrane column configuration shown in FIG. 6 is appropriate.

Thus, while we have illustrated and described the preferred embodiment of our invention, it is to be understood that this invention is capable of variation and modification, and we therefore do not wish to be limited to the precise terms set forth, but desire to avail ourselves of such changes and alterations which may be made for adapting the invention to various usages and conditions. Accordingly, such changes and alterations are properly intended to be within the full range of equivalents, and therefore within the purview, of the following claims.

Having thus described our invention and the manner and process of making and using it, in such full, clear, concise, and exact terms so as to enable any person skilled in the art to which it pertains, or with which it is most nearly connected, to make and use the same.

We claim:

1. A membrane system for treating a feed stream containing a fluid solution comprising at least two components to yield at least one product stream enriched in at least one component relative to the feed stream, said system comprising:
    (a) at least one continuous countercurrent membrane column having a high pressure side and a low pressure side;
    (b) a membrane selectively permeable to at least one component in the feed stream, said membrane extending through the cavity of said column to separate the high pressure side from the low pressure side;
    (c) high pressure feed means and low pressure feed means to selectively introduce the feed stream into the high and low pressure sides of said column; and
    (d) effluent means to selectively remove the product stream from the high and low pressure sides of said column.

2. A membrane system according to claim 1 wherein the membrane is a hollow fiber membrane.

3. A membrane system according to claim 1 which further comprises pumping means to allow reverse osmosis and selective refluxing of a portion of the effluent stream from the low pressure side of the membrane to the high pressure side of the column.

4. A membrane system according to claim 1 which further comprises recycle means for selectively diverting a portion of the effluent stream from the low pressure side of the column to the reactor which supplies the feed stream to the membrane system.

5. A membrane system according to claim 1 which further comprises a work-extracting means in the high pressure effluent stream to lower the pressure of the high pressure effluent stream and allow refluxing of a portion of the effluent stream from the high pressure side of the membrane column to the low pressure side of the column.

6. A membrane system according to claim 1 which further comprises valve means in the effluent stream of the high pressure side of the column for selectively diverting a portion of the effluent stream from the high pressure side of the column to the reactor which supplies the feed stream.

7. A membrane system according to claim 1 which further comprises at least one supplemental separation means for selectively treating the feed stream to the membrane system.

8. A membrane system according to claim 1 which further comprises at least one supplemental separation means for selectively treating at least one of the effluent streams of said membrane system.

9. A membrane system for treating a feed stream containing a fluid solution comprising at least two components to yield at least one product stream enriched in at least one component relative to the feed stream, said system comprising:
    (a) a first and a second continuous countercurrent membrane column arranged serially one to the other, each column having a membrane selectively permeable to at least one component in the feed stream to said column, said membrane extending through the interior cavity of the column to separate the column into a high pressure side and a low pressure side;
    (b) the first membrane column having an effluent stream on the low pressure side of the column, said stream becoming the feed stream to the high pressure side of said second membrane column;
    (c) the second membrane column having an effluent stream on the low pressure side of the column, said stream becoming the feed stream to the high pressure side of the first column;
    (d) pumping means in each of said effluent lines streams to cause the fluids in the streams to be pumped against a pressure gradient;
    (e) an effluent stream on the high pressure side of each column for withdrawing product enriched streams from said columns;

(f) means for selectively refluxing at least a portion of the product enriched stream from said columns to the low pressure side of the columns; and (g) a feed stream for introducing the fluid solution having at least two components to said system.

10. A membrane system according to claim 9 wherein the membrane in said first column is selectively permeable to at least one of the components in the first column effluent stream, and the membrane in said second column is selectively permeable to at least one of the components in the second column effluent.

11. A method for the integration of a countercurrent membrane column into a reverse osmotic countercurrent membrane separation system which comprises:

(a) determining whether the desired separation can be accomplished by utilizing a dual membrane separation column having a first membrane selectively permeable to at least one of the components in a first product stream and a second membrane selectively permeable to at least one of the principal components of a second product stream;

(b) determining whether the feed stream to said column contains a low or high concentration of the desired product components;

(c) determining whether the membrane will osmotically reject the desired product component;

(d) determining whether the product component stream may be refluxed back into the feed stream; and (e) selecting the appropriate integration design for the configuration of said system based upon the determination made in steps (a) to (d).

* * * * *